United States Patent
Shoher et al.

(10) Patent No.: US 6,382,980 B1
(45) Date of Patent: May 7, 2002

(54) COMPACT DENTAL MULTI-LAYERED MATERIAL FOR CROWN AND BRIDGE PROSTHODONTICS AND METHOD

(76) Inventors: Itzhak Shoher, 50 Sholomo Hamelech, St. Tel Aviv; Aharon Whitman, 13 JL Peretz, St. Petach Tikva, both of (IL)

( * ) Notice: Subject to any disclaimer, the term of this patent is extended or adjusted under 35 U.S.C. 154(b) by 0 days.

(21) Appl. No.: 09/531,379

(22) Filed: Mar. 21, 2000

(51) Int. Cl.[7] ................................................. A61C 5/08
(52) U.S. Cl. ........................ 433/223; 433/218; 164/97; 419/2
(58) Field of Search ................................ 433/206, 207, 433/218, 222.1, 223; 164/97; 419/2

(56) References Cited

U.S. PATENT DOCUMENTS

| | | | |
|---|---|---|---|
| 4,676,751 A | * | 6/1987 | Shoher et al. .............. 433/222 |
| 4,742,861 A | * | 5/1988 | Shoher et al. ................ 164/80 |
| 4,940,637 A | * | 7/1990 | Shoher et al. .............. 428/607 |
| 5,234,343 A | * | 8/1993 | Shoher et al. .............. 433/215 |
| 5,336,091 A | * | 8/1994 | Shoher et al. .............. 433/215 |
| 5,593,305 A | * | 1/1997 | Shoher et al. .............. 433/218 |
| 5,730,600 A | * | 3/1998 | Shoher et al. .............. 433/223 |

\* cited by examiner

*Primary Examiner*—Ralph A. Lewis

(57) ABSTRACT

A dental material and method for forming a laminated structure having at least three layers with at least one layer composed of a base material composition containing high fusing temperature metal particles and another layer composed of a filler material composition of low fusing temperature metal particles. The layers are arranged in tandem adjacent to one another in an alternating sequence such that upon firing of the laminated structure in a furnace at a temperature at least equal to the melting temperature of the low fusing temperature metal particles but below the melting temperature of the high fusing temperature metal particles diffusion occurs from the filler layers into the base layers to bring the base layers together and to form a solid structure.

17 Claims, 2 Drawing Sheets

COMPACT DENTAL MULTI-LAYERED MATERIAL FOR CROWN AND BRIDGE PROSTHODONTICS AND METHOD

FIELD OF THE INVENTION

This invention relates to a single compact dental material formed from laminated multiple metallic layers with at least two of the layers composed of different metal compositions in an alternating arrangement for use in forming a dental crown or bridge or for repairing a dental restoration and to a method of forming a dental coping from a single compact dental material in a single heat treatment.

BACKGROUND OF THE INVENTION

A metal coping is used in dentistry in the construction of a dental crown and/or bridge. The metal coping functions as the under structure of the crown and is usually covered, for reasons of aesthetics, with a fired-on coating of a ceramic porcelain composition or a polymer based veneering material. The metal coping supports the coating and provides the required structural strength and rigidity for the restored tooth to resist the forces of mastication.

A metal coping may be cast from an investment of a wax or plastic pattern of the tooth to be restored. An alternative procedure which does not require waxing, investing or casting and which currently has been gaining wide acceptance by many laboratory practitioners and dentists is to form the coping from a moldable dental material composition composed of a mixture of high and low fusing temperature metal particles, as disclosed, for example, in U.S. Pat. Nos. 5,234,343 and 5,332,622 respectively. The dental material as taught in these patents, the disclosure of which is herein incorporated by reference, forms a porous structure upon heat treatment having a high void volume of above at least 20%. Before heat treatment the dental material is molded into the shape of the tooth to be restored. The molded shape is self-supported and is converted upon heat treatment in a dental furnace into a porous structure essentially any without shrinkage. The heat treatment temperature must be sufficient to entirely or substantially melt the low fusing temperature metal particles but not the high fusing temperature metal particles. This results in the low fusing temperature metal particles interconnecting the high fusing temperature metal particles to form the porous structure without affecting the shape of the structure. The porous structure has a high void volume which is then filled to solidify the structure by adding a filler material of a metal or ceramic in a secondary heat treatment procedure.

In U.S. Pat. No. 5,593,305, the disclosure of which is herein incorporated by reference, it is further taught that the moldable dental material may be formed into a compacted strip formed of a base material of the high and low fusing temperature metal particles and wax. Likewise the filler material may also be in a compacted strip of the filler composition and wax. The strip of base material is hand molded over the surface of a die and heat treated followed by a similar procedure for the strip of filler material in a secondary heat treatment operation.

SUMMARY OF THE INVENTION

A dental material has been discovered in accordance with the present invention comprising a laminated structure of at least three layers with at least one of the layers composed of a base material composition containing high fusing temperature metal particles and with at least another layer comprising a filler material composition of low fusing temperature metal particles with said layers arranged adjacent to one another in an alternating sequence for forming a dental coping or for repairing a dental restoration upon firing the structure in a dental furnace at a temperature at least equal to the melting temperature of the low fusing temperature metal particles but below the melting temperature of the high fusing temperature metal particles. The dental material of the present invention is adapted to solidify upon heat treatment with the layers of filler material merging into the layers of the base material. The alternating arrangement of layers, the composition of the layers and the thickness of the layers control the degree of diffusion of the filler material into the layer(s) of base material. The diffusion occurs substantially simultaneous with the conversion of the base layer(s) into a porous structure. The layer(s) of filler material merge into the porous structure formed by the base material during heat treatment and solidify into a dental coping. The physical properties of the dental coping following heat treatment such as e.g., its hardness can be modified by variation of the composition and/or thickness of the layers. The arrangement of layers and their composition may also be varied to improve the adaptability of the surface layer to a fired-on coating of porcelain and/or to improve its adaptability to cementation.

It has been further discovered in accordance with the present invention that the laminated structure can be heat treated in a dental furnace in one firing, i.e., only one firing sequence, with the heat treatment carried out in stages either manually or automatically. Heretofore, it was essential for the base material composition to be physically separated from the filler material composition and for heat treatment to be carried out in at least two separate and distinct firing operations. Stated otherwise, heretofore it was essential to form a porous structure from the base material composition in one heat treatment operation before filler material could be added in a separate heat treatment operation to densify the porous structure.

The method of the present invention for forming a dental coping comprises the steps of: forming at least one sheet of a base material composition containing high fusing temperature metal particles and a wax binder; forming at least a second sheet of a filler material composition of low fusing temperature metal particles and a wax binder, laminating the sheet(s) of base material with the sheet(s) of filler material in an alternating sequence to form at least three laminated layers in which each sheet of base material lies adjacent to a sheet of filler material and selecting a thickness and binder concentration for each layer such that the layer(s) of filler material will impregnate the layer(s) of base material in one heat treatment operation and cause the layers of base material to converge.

BRIEF DESCRIPTION OF THE DRAWINGS

Additional advantages of the present invention will become apparent from the following detailed description of the invention when read in conjunction with the accompanying drawings of which.

DETAILED DESCRIPTION OF THE INVENTION

Figure 1A:
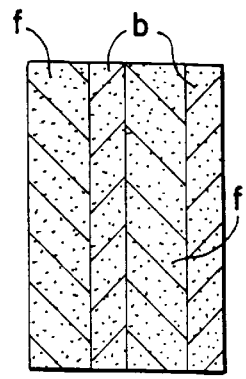
FIG. 1a is an enlargement of the laminated layers of the dental material of FIG. 1.
Figure 1:
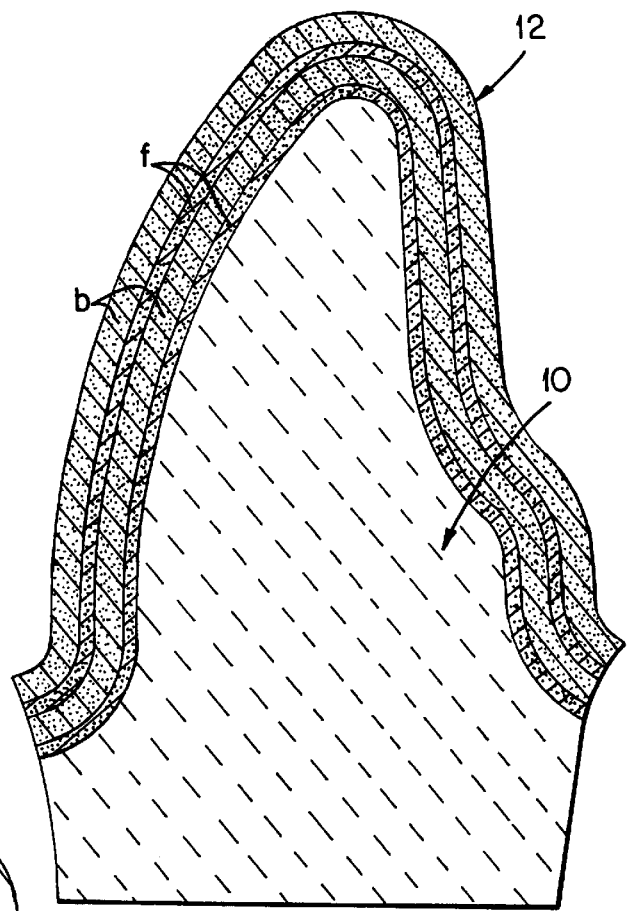
FIG. 1 is a cross sectional view of one embodiment of the dental material of the present invention shown molded over a dental die of a tooth to be restored before heat treatment.
Figure 2:
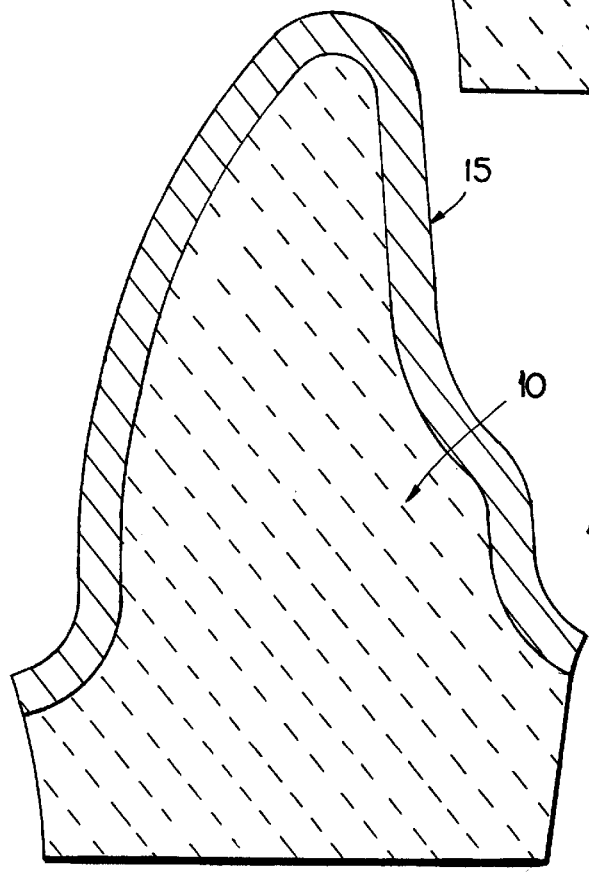
FIG. 2 is a cross sectional view of the solidified dental material structure of FIG. 1 after heat treatment but before removal from the die.

Referring now to FIGS. 1 and 2 showing a dental die 10 in cross section having an external shape conforming to the tooth to be restored upon which is molded the dental material 12 of the present invention. The dental material 12 is a laminated multi-layered structure which conforms to the shape of the die 10 and comprises at least three layers with at least two of the layers composed of different metallic particle compositions identified as layers "b" and "f" respectively. The layer b constitutes the base material and comprises a metal composition formed of high fusing temperature metal particles and a volatile binder. The volatile binder is preferably a wax composition. The base material may be composed essentially of high fusing temperature metal particles and a binder or may be an aggregate mixture of high fusing temperature metal particles and low fusing temperature metal particles held together by the wax binder. The concentration of the binder may vary widely although preferably between about twenty percent by volume and up to eighty percent by volume of the base material composition. Any wax may be used which is relatively soft and tacky to form the binder and may be selected from any natural wax, mineral wax, or organic wax composition. The binder should melt relatively cleanly without leaving a significant residue at a melting temperature well below or at least no higher than the melting temperature of the low-fusing temperature metal particles.

The base material layer "b" of high-fusing temperature metal particles may be selected from a single metal or metal alloy, preferably of precious metals such as platinum and palladium in any desired proportion relative to one another from zero to one hundred percent. Additional constituents may be added such as gold, silver, copper, magnesium, aluminum, zinc, gallium, indium and other metals selected from the third, fourth or fifth group of elements of the periodic table. The total weight percent of the elements other than gold, silver, and the platinum, group metals should not exceed ten percent. Gold may be added in any proportion to the high-fusing temperature metal component to increase the affinity of the high-fusing temperature metal component to the low-fusing temperature metal components or to itself in the absence of other low fusing component. In the latter instance gold may represent a major constituent of the high fusing metal composition and depending upon its concentration may substantially lower the melting temperature of the high fusing component.

The layer "f" constitutes a filler material composition of low fusing temperature metal particles composed preferably of gold or a gold alloy, with gold as the major constituent. The preference for gold as the major constituent of the low-fusing filler material "f" is based on its known characteristics of workability, biocompatibility, non-oxidizing properties and color. The layer of filler material "f" must possess a melting temperature below that of the high fusing temperature metal particles in the base material composition.

In FIG. 1, and preferably as shown enlarged in FIG. 1a, the layers "b" and "f" lie adjacent to one another in an alternating arrangement with the filler material layer "f" selected as the outer layer of the composite tandem arrangement of layers of the dental material 12. For illustrative purposes the laminated arrangement shown in FIG. 1 has four layers with two "b" layers and two "f" layers. However, it should be understood that any number of layers above three can be formed to any desired number. In fact, an arrangement of numerous alternating layers may be advantageous for forming a homogeneous structure and to control the filling of voids.

A dental coping 15 is formed, as shown in FIG. 2 when the dental material 12 of FIG. 1 is subjected to heat treatment in a dental furnace at a temperature at least equal to the melting temperature of the low fusing temperature metal particles of the filler material composition but below the melting temperature of the high fusing temperature metal particles in the base material composition. The wax binder is volatile and vaporizes at a temperature during heat treatment below the melting temperature of the low fusing temperature metal particles. The filler material layers "f" of FIG. 1 impregnate the base material layers "b" during heat treatment forming a unified single solidified dental coping 15 when removed from the die 10.

During heat treatment the particles of the low fusing temperature metal in the filler layer(s) "f" must melt and diffuse into the base material layer(s) "b" to cause the base material layers "b" to converge. Moreover, this must occur without any significant shrinkage in the structure 15 so that the structure 15 has a shape closely approximating the molded shape of the dental material 12 before heat treatment. This is accomplished in accordance with the present invention by selecting a thickness and binder concentration for each layer such that the layer(s) of filler material "f" will impregnate the layer(s) of base material "b" in one heat treatment operation. The variables affecting the degree of diffusion and impregnation depend upon thickness, material composition and binder concentration in the layers. The concentration of the filler material separating said layers of base material must be sufficient by volume to permit diffusion of the melted filler particles into the base material layers upon heat treatment. If insufficient concentration of filler material exists the void volume of the base material will not be completely filled up during heat treatment leaving a structure which is still porous. Alternatively excess concentration of filler material will result in a structure having bands or layers of solidified filler material. Both situations can be used advantageously in accordance with the present invention by selecting specified filler material layers "f" in the laminated arrangement to have either insufficient or excess concentrations of filler material by volume relative to the volume of adjacent layers of base material. The concentration of filler material is varied by the thickness of the layer of filler material and the concentration of binder in the filler material layer.

The relative thickness of the adjacent base material layer (s) and the concentration of binder in the base material layer(s) affect the diffusion of filler material by controlling the porosity of the base layer upon heat treatment, i.e., its void volume and capacity to be impregnated with filler material. Accordingly, the thickness and concentration of binder in the base material layers "b" can be varied to accommodate the diffusion of the filler material particularly so that only one heat treatment firing is necessary to cause the base layer "b" to be infiltrated with filler material and to solidify without shrinkage.

In addition to varying the thickness of the layers and the concentration of binder it should be understood that neither the base layers "b" nor the filler layers "f" need be of identical composition. In fact, the composition of the base layer "b" and the composition of filler layers "f" may vary to enhance the properties of the heat treated coping 15 as well as to cause the outer and/or inner surface of the structure 15 to be different in composition and density.

Moreover, although only one heat treatment operation is required it can be performed at a single temperature setting or using more than one temperature setting and in staged succession which can either be manual or automated to control the diffusion and impregnation of the low fusing metal particles in the layers "f" into the high fusing temperature layers "b".

The molding of the dental material 12 on the die 10 is explained in the aforementioned patents as well as in U.S. Pat. No. 5,730,600 the disclosure of which is herein incorporated by reference. However, it should be understood that in accordance with the present invention only one laminated multi-layered dental material structure 12 is needed to both form a porous body from the "b" layer(s) of high fusing metal composition and to impregnate and densify the porous body by melting and diffusing the layer(s) "f" of filler material forming a solid structure 15. This occurs substantially simultaneously in successive stages during the single heat treatment firing operation.

Figure 3:
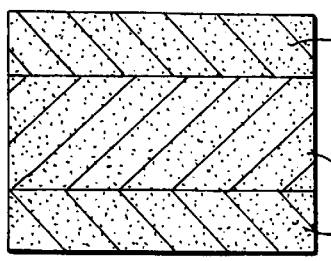
FIG. 3 is a cross sectional view of a laminated three layer composite of the dental material of the present invention before heat treatment.
Figure 3A:
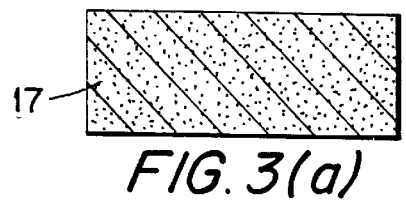
FIG. 3a is a cross sectional view of the solidified structure of FIG. 3 after heat treatment.
Figure 4:
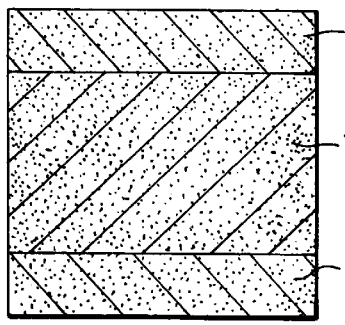
FIG. 4 is a cross sectional view of an alternate arrangement of a laminated three layer composite of the dental material of the present invention before heat treatment.
Figure 4A:
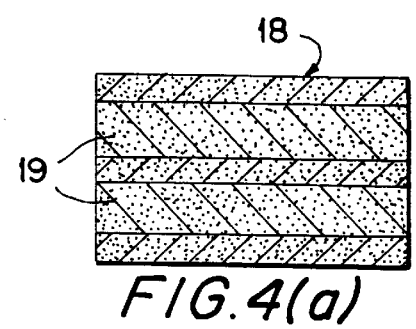
FIG. 4a is a cross sectional view of the solidified structure of FIG. 4 after heat treatment.
Figure 5:
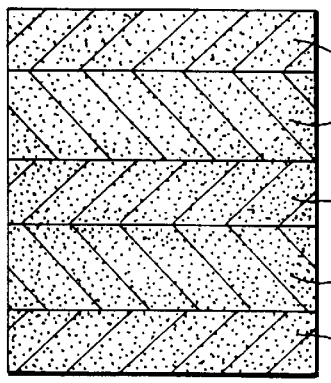
FIG. 5 is another cross sectional view of an alternate arrangement of a laminated five layer composite of the dental material of the present invention before heat treatment.
Figure 5A:
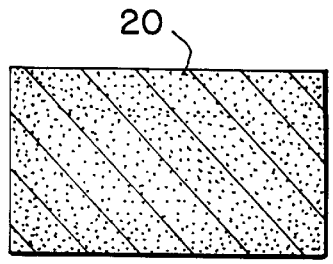
FIG. 5a is a cross sectional view of the solidified structure of FIG. 5 after heat treatment.
Figure 6:
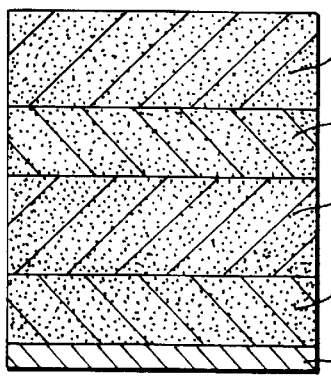
FIG. 6 is yet another cross sectional view of an alternate arrangement of a laminated five layer composite of the dental material of the present invention before heat treatment.
Figure 6A:
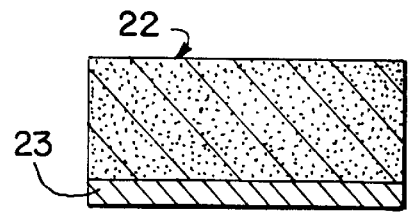
FIG. 6a is a cross sectional view of the solidified structure of FIG. 5 after heat treatment.

FIGS. 3 through 6 illustrate alternative embodiments of the invention. FIG. 3 shows a three layer laminated body with an outer and inner layer of base material "b" respectively. The thickness of the filler material layer "f" is selected to provide a volume of filler material which will cause complete diffusion of the filler material into the base material layers "b" for forming a single solidified body 17 as shown in FIG. 3a. FIG. 4 also shows a three layer laminated body with an outer and inner layer of base material "b" separated by a much thicker layer of filler material "f". In the arrangement of FIG. 4 an excess of filler material by volume exists resulting in a solidified structure 18 as shown in FIG. 4a having layers or bands 19 of solidified filler material following heat treatment. Alternatively, if insufficient filler material existed a solidified body would have been formed with substantially greater porosity than the structure 17 of FIG. 3a. However, an unfilled or partially filled base material layer "b" may be desirable to render the outer and inner surfaces of the coping more adaptable for porcelain firing and for cementation. FIG. 5 shows an arrangement of five alternating layers with the outer and inner layers composed of a filler material composition "f". In this arrangement the diffusion of filler material into the base material layers "b" are controlled through opposite adjacent sides of the base material layer "b" to cause more uniform diffusion of filler material in forming the solidified structure 20 as shown in FIG. 5a. FIG. 6 is yet an alternative arrangement of a five layer laminated body having two base material layers "b" and two filler material layers "f" and a fifth layer of a different base material composition "b1" from the other base material layers "b". This different base material composition "b1" may include different size high fusing temperature metal particles from that in layers "b" so as to produce a roughened surface for cementation and/or may include additional metallic constituents to achieve this objective. The solidified structure 22 as shown in FIG. 6a is formed with a surface 23 having different physical characteristics from the physical characteristics in the rest of the solidified structure 22.

The dental material 12 may be formed into a laminated body in any conventional fashion such as by cladding one layer upon another with the laminated body compressed into a compacted strip of any desired geometry. During this procedure, especially when the layers are cladded and compressed, particles from one type of layer or from each type of layer may infiltrate into the other during compression i.e., particles from the "f" layers for example, may be physically incorporated into the "b" layers and vice versa particularly at their borders making it difficult to distinguish the different layers of the laminated structure from one another. Stated otherwise the border between the layers become "fuzzy". It should, however, be understood that the layers may always be distinguished from one another by analyzing their major constituents.

The thickness of the compressed laminated body may lie between 50 and 2000 microns, depending upon the specific application, with a thickness of between 100 to 500 microns preferred when forming a dental coping.

It should further be understood that the dental material of the present invention although primarily intended for forming a dental coping may also be used for repair work, to join restorations at the interproximal and to form a bridge structure.

What is claimed:

1. A dental material comprising a laminated structure of at least three layers with at least one of the layers composed of a base material composition containing high fusing temperature metal particles and with at least another layer comprising a filler material composition of low fusing temperature metal particles with said layers arranged in tandem adjacent to one another in an alternating sequence for forming a dental coping and/or for repairing a dental restoration upon firing the laminated structure in a furnace at a temperature at least equal to the melting temperature of the low fusing temperature metal particles in the filler material composition but below the melting temperature of the high fusing temperature metal particles in the base material composition.

2. A dental material as defined in claim 1 wherein each layer of said base material composition and each layer of said filler material composition includes a volatile binder.

3. A dental material as defined in claim 2 wherein said volatile binder comprises wax.

4. A dental material as defined in claim 3 wherein said high-fusing temperature metal particles in said base material composition comprise precious metals and alloys thereof selected from the group consisting of platinum and palladium in a proportion relative to one another of from zero to 100% alone or in combination with a precious metal or precious metal alloy selected from the group consisting of gold, silver, copper, magnesium, aluminum, zinc, gallium, indium and other metals from the third, fourth or fifth group of elements of the periodic table.

5. A dental material as defined in claim 4 wherein said low-fusing temperature metal particles in said filler material composition comprises gold or a gold alloy as the predominant or at least major constituent thereof.

6. A dental material as defined in claim 5 wherein said laminated structure comprises at least two layers of said base material composition separated by said filler material composition.

7. A dental material as defined in claim 6 wherein the filler material separating said layers of base material is sufficient in concentration by volume to diffuse into the base material layers upon said heat treatment so that the layers of base material converge.

8. A dental material as defined in claim 6 wherein said laminated structure further comprises at least two layers of said filler material composition.

9. A dental material as defined in claim 8 comprising at least five alternating layers of base material composition and filler material composition arranged in tandem having an outer layer of said filler material composition.

10. A dental material as defined in claim 8 wherein said four alternating layers are arranged in tandem and further comprising an additional layer of a modified base material composition forming the inner layer of said tandem arrangement.

11. A dental material as defined in claim 5 wherein said laminated structure comprises at least two layers of said filler material composition separated by said base material composition.

12. A dental material as defined in claim 5 wherein said laminated structure comprises compressed multiple layers forming indistinct borders between at least some of the layers.

13. A method for forming a dental coping comprising the steps of:

forming at least one sheet of a base material composition comprising high fusing temperature metal particles and a wax binder; forming at least a second sheet of a filler material composition of low fusing temperature metal particles and a wax binder, laminating the sheet(s) of base material with the sheet(s) of filler material in an alternating sequence to form at least three laminated layers in which each sheet of base material lies adjacent to a sheet of filler material and selecting a thickness and binder concentration for each layer such that the layer(s) of filler material will impregnate the layer(s) of base material in one heat treatment operation at a temperature at least equal to the melting temperature of the low fusing temperature metal particles in the filler material composition but below the melting temperature of the high fusing temperature metal particles in the base material composition.

14. A method for forming a dental coping as defined in claim 13 wherein the temperature of said heat treatment increases in stages but in one firing.

15. A method for forming a dental coping as defined in claim 14 having at least two layers of base material wherein the filler material separating said layers of base material is selected to be sufficient in concentration by volume to diffuse into said base material layers upon said heat treatment to cause said base layers to converge.

16. A method for forming a dental coping as defined in claim 14 having at least two layers of base material wherein the concentration of filler material by volume separating said layers of base material is in excess of the void volume formed in the base layers during heat treatment such that the coping structure being formed following heat treatment is non-homogeneous in density and contains bands having different void volume percentages.

17. A method for forming a dental coping as defined in claim 13 having a multiple number of layers compressed together into a single structure wherein the borders between at least some of the layers are indistinct.

* * * * *